(12) United States Patent
Smith

(10) Patent No.: US 7,418,880 B1
(45) Date of Patent: Sep. 2, 2008

(54) SAMPLE COLLECTOR USING A SYRINGE WITH A SIDE PORT IN THE BARREL

(76) Inventor: Michael P Smith, 3520 S. Rolling Oaks Dr., Tulsa, OK (US) 74107-4515

( * ) Notice: Subject to any disclaimer, the term of this patent is extended or adjusted under 35 U.S.C. 154(b) by 377 days.

(21) Appl. No.: 11/164,997

(22) Filed: Dec. 13, 2005

Related U.S. Application Data

(60) Provisional application No. 60/635,557, filed on Dec. 13, 2004.

(51) Int. Cl.
*B01L 3/02* (2006.01)
*A61M 5/31* (2006.01)

(52) U.S. Cl. ............ 73/864.01; 73/864.13; 73/864.51; 73/864.91; 604/264; D24/114; D24/130

(58) Field of Classification Search .................. 73/863, 73/864, 864.01, 864.02, 864.86, 864.87, 73/864.13, 864.51, 864.91; 206/364, 571; 604/6.12, 187, 264; D24/112, 114, 130
See application file for complete search history.

(56) References Cited

U.S. PATENT DOCUMENTS

| | | | | |
|---|---|---|---|---|
| 2,541,621 A | * | 2/1951 | Thompson | 604/92 |
| 4,340,056 A | * | 7/1982 | Erb | 604/82 |
| 4,549,554 A | * | 10/1985 | Markham | 600/566 |
| 4,995,867 A | * | 2/1991 | Zollinger | 604/514 |
| 2002/0025581 A1 | * | 2/2002 | Schmidt et al. | 436/180 |
| 2002/0198498 A1 | * | 12/2002 | Porat et al. | 604/187 |
| 2004/0131506 A1 | * | 7/2004 | Zurcher | 422/102 |

* cited by examiner

*Primary Examiner*—David A. Rogers
(74) *Attorney, Agent, or Firm*—Head, Johnson & Kachigian, P.C.

(57) ABSTRACT

A modified syringe collects samples of a fluid without removing volatile compounds by forming a vacuum within a sample collection vial. A fluid sample is drawn into the collection vial by means of the applied vacuum.

12 Claims, 2 Drawing Sheets

SAMPLE COLLECTOR USING A SYRINGE WITH A SIDE PORT IN THE BARREL

CROSS-REFERENCE TO RELATED APPLICATIONS

This application claims priority to U.S. Provisional Application Ser. No. 60/635,557, filed Dec. 13, 2004.

BACKGROUND OF THE INVENTION

1. Field of the Invention

The present invention relates to a device and method for rapidly and efficiently acquiring a sample of a fluid. Specifically, the device and method provides a sample container in which a vacuum is created. The sample is then rapidly sucked into the container by the vacuum thereby avoiding loss of volatiles in the solution and alteration of its chemical composition.

2. Background

In many fields it is necessary to routinely take samples of various fluids to determine their chemical composition. It is often necessary to determine the precise chemical make up of a fluid including the gases and volatile components of the sample. This is especially true in the petroleum industry in which mud and other fluid samples are routinely taken to measure various data.

Various methods have been developed for obtaining samples to be tested. One common method is to simply use a syringe to suck fluid into it and subsequently deposit it into a sample vial. The physical action of this often results in the removal of especially volatile compounds from the fluid. This alters the chemical composition of the sample and provides for less accurate readings.

It is therefore desirable to provide a device and method for collecting a fluid sample without substantially removing volatiles therefrom.

SUMMARY OF THE INVENTION

A new simple sampling device collects and seals volatile fluid samples without volatile loss in a single simultaneous operation. Fluid samples that can benefit from sampling using this sampling device include, but are not limited to, environmental water and air samples and drilling mud from oil and gas exploration and production wells.

The sampling device consists of a hermetically sealed sample bottle, or other suitable hermetically sealed container such as a can, sampling bag, or any other appropriate container. The hermetically sealed sample bottle or other suitable hermetically sealed container must have a septum, or other appropriate device, that allows a needle to be introduced and removed from the container.

Prior to collecting the fluid sample, the hermetically sealed sample bottle, or other suitable hermetically sealed container, can simply contain air, or can be filled with any other type of gas, or can be evacuated. Any desired agent that can be of benefit to maintaining sample quality, or have any other desired purpose, can be added to the sample bottle prior to sealing.

The sampling device also consists of a syringe with a side port, or opening, and a needle. The volume of fluid sampled is determined by the size of the syringe, the placement of the side port on the syringe, and the pressure inside the sample bottle.

A fluid sample is collected using the following steps. First, the plunger on the syringe is inserted and pushed into the body of the syringe as far as possible. Second, the needle on the syringe is inserted into the sample bottle through the septum. Third, the syringe is partly or completely submerged into the fluid to be sampled so that the side port on the syringe is completely submerged in the said fluid. Fourth, the plunger on the syringe is retracted until the sealing mechanism at the end of the syringe passes part of the side port, it is not necessary for the seal to pass by the entire side port.

The fourth step of retracting the plunger results in the sample bottle or other suitable container to be filled with the desired volume of fluid. A vacuum is generated in the sample bottle by the initial retracting of the plunger. The vacuum in the sample bottle is generated before the seal at the end of the plunger reaches the side port on the syringe.

The sample bottle is filled with the desired volume of fluid when the plunger is retracted to the point that the seal at the end of the plunger passes the lowest terminus of the side port. The vacuum generated by the initial retraction of the plunger causes the fluid to enter the bottle through the side port, into the body of the syringe, and through the needle into the sampling bottle.

The process of filling the sealed bottle with fluid is extremely fast, taking only a fraction of a second. The very short time required to capture a sealed sample aids in the capture of a representative fluid sample having the same composition as the body of fluid being sampled.

Sampling is completed by removing the bottle from the needle on the syringe.

Other means, not described here, of sampling fluids with syringes, or other devices that generate a vacuum, can be problematic. The vacuum used to suction the sample into these other means can cause the removal of volatiles from the fluid. Such volatiles can include benzene, MTBE, and other volatiles from environmental water samples, or light hydrocarbon and non-hydrocarbon gases such as methane, ethane, and carbon dioxide from oil and gas well drilling mud. These other sampling means usually require transferring the sample from a syringe or other sampling device to another container, providing additional time and opportunity for compositional change to the fluid sample.

The sampling means described herein is designed to obtain a sample that has the same composition as the body of fluid sampled. The fluid sampling means described herein preserves the volatiles in the sample as the vacuum is generated in the sample container itself. There is no transfer of the fluid sample after sampling, as the fluid is collected directly into the sampling bottle. Sampling time is very short, reducing the possibility of compositional change of the fluid sample. The fluid sample can be analyzed directly from the sampling bottle eliminating the possibility of compositional changes incurred by handling the sample in the laboratory.

The bottle can be completely filled with fluid, if the bottle is pre-evacuated before sampling.

The bottle can also be partly filled with fluid, and partly left unfilled. The amount of filling is reproducible and can be pre-determined by the initial pressure in the bottle, the size of the bottle and the syringe, and the placement of the side port on the syringe.

The ability to partially fill sample bottles, as described herein, is a distinct advantage over simply opening a bottle under the surface of a fluid and resealing, as that process results in only completely filled bottles. Partly filled bottles are useful to analyses of volatiles in the fluid. The volatiles can be analyzed using vacuum extraction of head space gas, and vacuum extraction of volatiles in the liquid that enter the gas phase under vacuum. This gas can then be analyzed by known techniques such as mass spectrometry or gas chromatography.

Filling the sampling bottle submerged below the surface of the fluid can be a distinct advantage over collecting a surface fluid sample. Collecting submerged fluid samples in pre-sealed bottles, as described herein, allows chemical profiling of fluids as a function of depth in the body of fluid. Volatiles in fluids can degas at the surface of a liquid, but may be present in a fluid sample that is collected submerged. Also, the composition of fluids may vary with depth and latitude and longitude in bodies of fluid, such as in oceans, lakes, environmental monitoring wells, mud pits on oil and gas wells, septic tanks, and other bodies of fluids. In many cases it can be useful to study the compositional variations within such bodies of fluids.

Volatiles in the fluids can be analyzed directly from the partly filled sampling bottles, thus eliminating any volatile loss or other sample degradation caused by re-sampling.

Liquids in completely filled bottles can also be directly analyzed using techniques such as liquid chromatography.

Filled or partly filled sample bottles can also be sub-sampled for multiple analyses, if desired or necessary. Sub-sampling can be performed using a syringe and passing its needle through the septum of the hermetically sealed sample bottle.

Use of pre-sealed sample bottles allows enhanced quality control over sealing in the field, providing greater insurance of volatile retention. It can also be difficult to hermetically seal bottles in the field if submerged in a fluid rich in solids, such as oil and gas well drilling mud.

Pre-sealing of crimp-sealed bottles eliminates the need to provide expensive and complicated crimping apparatus to multiple field locations. Affecting a good crimp-seal can be difficult by an inexperienced technician, or in difficult or dirty field conditions, such as on oil and gas wells.

Extensions can be added to the syringe body and plunger to allow samples to be taken in hard to reach locations, such as environmental monitoring wells at gasoline filling stations, or sampling water at various depths in a lake.

Triggering mechanisms can be added to the sampling device to permit sampling without an operator present under predetermined conditions. These conditions could include such factors as time, date, depth, temperature, amount of precipitation, traffic flow through a gasoline filling station, or any other desired criteria.

The process can be automated. Those skilled in the art will appreciate that there are many devices for automating the actuation of a syringe. Most consist of a piston device attached to the plunger and a motor. The motor may be actuated by a simple switch mechanism or may be operated by a computer that may be timed.

DETAILED DESCRIPTION OF THE PREFERRED EMBODIMENTS

The embodiments discussed herein are merely illustrative of specific manners in which to make and use the invention and are not to be interpreted as limiting the scope of the instant invention.

While the invention has been described with a certain degree of particularity, it is to be noted that many modifications may be made in the details of the invention's construction and the arrangement of its components without departing from the spirit and scope of this disclosure. It is understood that the invention is not limited to the embodiments set forth herein for purposes of exemplification.

Figure 1:
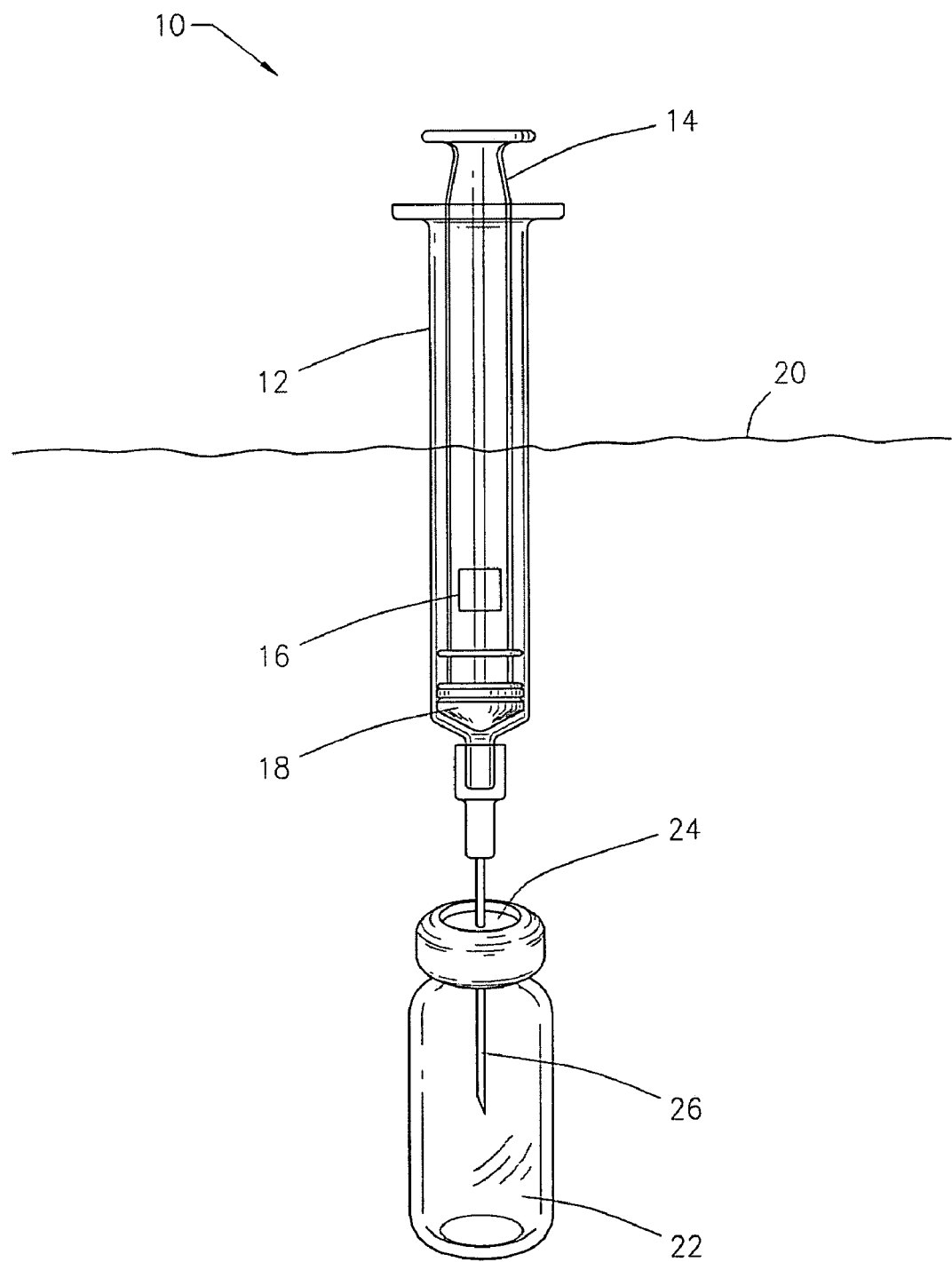
FIG. 1 shows a side view of a preferred embodiment of the invention.

FIG. 1 shows fluid sample collecting device 10 just prior to collection of a sample. Device 10 consists of a syringe 12 having a needle 26. Plunger 14 fits inside syringe 12 and has rubber seal 18 at the end of it. Those skilled in the art will realize that the seal at the end of the plunger may be comprised of rubber, an elastomer or other material so long as it forms an air tight seal with the inside wall of the plunger. Syringe 12 can be any of various sizes and is a typical syringe known in the art. One distinguishing feature of device 10 is side port 16. Side port 16 is an opening in the side of syringe 12. In this particular embodiment, side port 16 is rectangular. However, those skilled in the art will appreciate that side port 16 may be comprised of any geometry, but should not be so small that a vacuum is applied to liquid entering it. Vacuum should only be applied to the sample by the sample bottle. Needle 26 is inserted through septum 24 into empty bottle 22. Bottle 22 and syringe 12 are placed partially below the surface of a fluid 20 from which a sample is to be taken. The syringe need only be placed far enough into the fluid such that side port 16 is completely submerged.

To collect a sample, the plunger 14 is pulled upward. This causes a vacuum to form inside the fluid sample bottle. When the rubber seal at the end of the plunger is pulled past side port 16, the vacuum inside the sample bottle 22 is exposed to the fluid that the sampling device has been placed in. This causes a fluid sample to rush through the side port and into the collection bottle 22.

Figure 2:
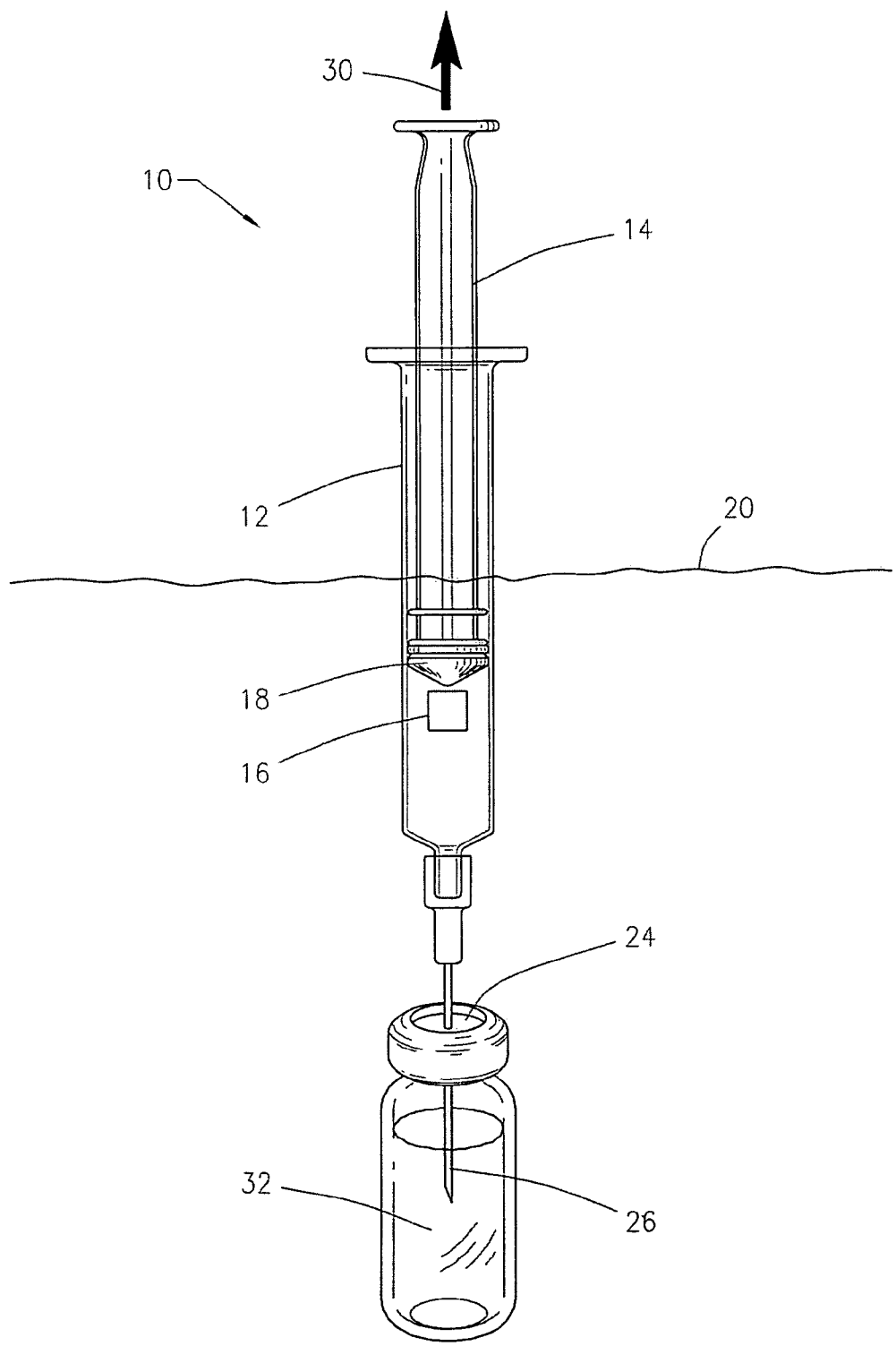
FIG. 2 shows a side view of a preferred embodiment of the invention after a fluid sample has been taken.

FIG. 2 shows the sampling device 10 after a sample has been taken. Plunger 14 has been lifted in the direction of arrow 30 while the syringe 12 is remained stationary. Plunger seal 18 has been lifted past side port 16. Because only a partial vacuum was formed in bottle 22, the bottle is only partially filled with sample fluid 28. It is often desirable to not fill bottle 22 all the way with sample. The amount of fluid collected in sample collection bottle 22 is dependent on how high up on syringe 12 side port 16 is located. The higher side port 16, the greater vacuum formed in bottle 22 and therefore the larger the amount of sample 32 collected.

The device as shown rapidly and efficiently collects a fluid sample with a minimum of mechanical or other interference of the sample. This prevents volatiles, gases and other chemicals from being removed from the sample. The sample therefore is more accurate and more representative of the contents of the fluid being sampled.

In the illustrated embodiment, a syringe is used in conjunction with a rubber seal to hermetically seal the sample bottle to the syringe. Those skilled in the art will appreciate that there are other methods to hermetically seal the syringe to the sample bottle. A bottle top that may be screwed or snapped on to the top of the bottle having a tube that connects to the syringe could also be used. Any means that allows the syringe to be hermetically sealed to the sample bottle will work with the present invention.

Whereas, the present invention has been described in relation to the drawings attached hereto, it should be understood that other and further modifications, apart from those shown or suggested herein, may be made within the spirit and scope of this invention.

What is claimed is:

1. A method for collecting a liquid sample, comprising the steps of;
   inserting a needle of a syringe while a plunger is substantially depressed into a sample bottle;
   inserting the sample bottle and the syringe into a liquid such that a side port on the syringe is fully submerged in the liquid; and
   withdrawing the plunger from the syringe such that the plunger rises above the side port, thereby creating a vacuum within the sample bottle which draws some of the liquid through the side port and into the sample bottle.

2. The method for collecting a liquid sample of claim 1 wherein the sample bottle includes a hermetically sealing septum.

3. The method for collecting a liquid sample of claim 1 wherein an end of the plunger of the syringe includes a seal.

4. The method for collecting a liquid sample of claim 1 wherein the steps of the method for collecting the liquid sample are automated.

5. The method for collecting a liquid sample of claim 1 further comprising the step of adding at least one extension to the syringe and plunger for collecting the liquid sample in hard to reach locations.

6. A method for collecting a fluid sample, comprising the steps of:
   inserting a needle of a syringe into a hermetically sealing septum of a fluid sample bottle;
   submerging the fluid sample bottle and a side port on the syringe into a fluid;
   collecting a fluid sample by withdrawing a plunger from the syringe above the side port of the syringe such that the fluid sample is drawn through the side port and into the fluid sample bottle.

7. The method for collecting a fluid sample of claim 6 wherein the step of inserting the needle of the syringe into the fluid sample bottle further comprises inserting the needle of the syringe into the sealing septum of the fluid sample while the plunger is substantially depressed within the syringe.

8. The method for collecting a fluid sample of claim 6 wherein the step of collecting the fluid sample further comprises withdrawing the plunger having a seal at one end from the syringe above the side port of the syringe to create a vacuum within the fluid sample bottle such that the fluid sample is drawn through the side port and into the fluid sample bottle.

9. The method for collecting a fluid sample of claim 6 wherein the steps of the method for collecting the fluid sample are automated.

10. The method for collecting a fluid sample of claim 6 further comprising the step of adding at least one extension to the syringe and plunger for collecting the fluid sample.

11. The method for collecting a fluid sample of claim 6 wherein the fluid to be sampled is selected from the group consisting of a fluid rich in solids, a mixture, a slurry or a suspension.

12. The method for collecting a fluid sample of claim 11 wherein the fluid to be sampled is oil or drilling mud.

* * * * *